US00PP27150P2

(12) United States Plant Patent
Yates

(10) Patent No.: US PP27,150 P2
(45) Date of Patent: Sep. 13, 2016

(54) ***BEGONIA* PLANT NAMED 'YASPYELL'**

(50) Latin Name: ***Begonia* hybrid**
Varietal Denomination: YASPYELL

(71) Applicant: Frederic C. Yates, Congleton (GB)

(72) Inventor: Frederic C. Yates, Congleton (GB)

(73) Assignee: Florensis B.V., Hendrik-Ido-Ambacht (NL)

( * ) Notice: Subject to any disclaimer, the term of this patent is extended or adjusted under 35 U.S.C. 154(b) by 266 days.

(21) Appl. No.: 14/120,032

(22) Filed: Apr. 16, 2014

(51) Int. Cl.
*A01H 5/02* (2006.01)

(52) U.S. Cl.
USPC ..... Plt./343

(58) Field of Classification Search
USPC ..... Plt./343
See application file for complete search history.

*Primary Examiner* — Keith Robinson
(74) *Attorney, Agent, or Firm* — Penny J. Aguirre

(57) ABSTRACT

A new cultivar of hybrid *Begonia*, 'YASPYELL', that is characterized by its large flowers that are yellow in color, its semi-double sterile male flowers and single female flowers (with one or two extra tepals), its flowers with broad tepals, its flowers that have a high degree of forward and horizontal facing flowers, its compact and well-branched habit without cane production in its first year of growth, and its foliage that is medium green in color.

2 Drawing Sheets

Botanical classification: *Begonia* hybrid.
Cultivar designation: 'YASPYELL'.

RELATED APPLICATIONS

This application is related to U.S. Plant Patent applications filed for cultivars derived from the same breeding program entitled *Begonia* Plant Named 'YASPRINK' (U.S. Plant Pat. No. 23,266), 'YASPWHIT' (U.S. Plant Pat. No. 23,281), and *Begonia* Plant Named 'YASPED' (U.S. Plant Pat. No. 22,412).

BACKGROUND OF THE INVENTION

The present invention relates to a new and distinct cultivar of *Begonia* plant, botanically a hybrid that includes *Begonia boliviensis* hybrids in its parentage. The new cultivar is known as *Begonia* 'YASPYELL' and will be referred to hereafter by its cultivar name, 'YASPYELL'. 'YASPYELL' is a new cultivar of *Begonia* that is particularly useful for use in flowerbeds, containers, and hanging baskets.

The new cultivar was derived from a controlled breeding program conducted by the Inventor at his nursery in Congleton, Cheshire, United Kingdom. The overall purpose of the breeding program is to make selections of *Begonia* plants that perform well as basket and patio plants. 'YASPYELL' was selected in the Inventor's greenhouse in July of 2008 as a single unique plant from amongst the seedlings derived from a cross made in June of 2007 between unnamed *Begonia* plants of hybrid origin from the Inventor's breeding program as the female and male parents.

Asexual propagation of the new cultivar was first accomplished by stem tip cuttings in Congleton, Cheshire, United Kingdom in July of 2008 by the Inventor. Asexual propagation by stem tip cuttings has determined that the characteristics of the new cultivar are stable and are reproduced true to type in successive generations.

SUMMARY OF THE INVENTION

The following traits have been repeatedly observed and represent the characteristics of the new cultivar, which in combination distinguish 'YASPYELL' as a new and distinct cultivar of *Begonia*.

1. 'YASPYELL' exhibits large flowers that are yellow in color.
2. 'YASPYELL' exhibits semi-double sterile male flowers and single female flowers (with one or two extra tepals).
3. 'YASPYELL' exhibits flowers with broad tepals.
4. 'YASPYELL' exhibits flowers that have a high degree of forward and horizontal facing flowers.
5. 'YASPYELL' exhibits a compact and well-branched habit without cane production in its first year of growth.
6. 'YASPYELL' exhibits foliage that is medium green in color.

The female differs from 'YASPYELL' in having pale pink to rose colored flowers. The male parent of 'YASPYELL' differs from 'YASPYELL' in having pinkish red flowers. 'YASPYELL' can be most closely compared to cultivars from the same breeding program: 'YASPWHIT', 'YASPRINK', and 'YASPED'. 'YASPWHIT' differs from 'YASPYELL' in having white flowers lightly flushed with pink. 'YASPRINK' differs from 'YASPYELL' in having pink flowers. 'YASPED' differs from 'YASPYELL' in having dark red flowers, a more pendulous plant habit and in having a more vigorous growth habit.

BRIEF DESCRIPTION OF THE DRAWINGS

The accompanying colored photographs illustrate the overall appearance and distinct characteristics of the new *Begonia*.

The photograph In FIG. 1 was taken of a plant approximately three months in age (4 cuttings per 15-cm container) that was grown in an unheated greenhouse under ambient light in Congleton, Cheshire, United Kingdom. The photograph in FIG. 1 provides a side view of 'YASPYELL' in bloom.

Figure 1:
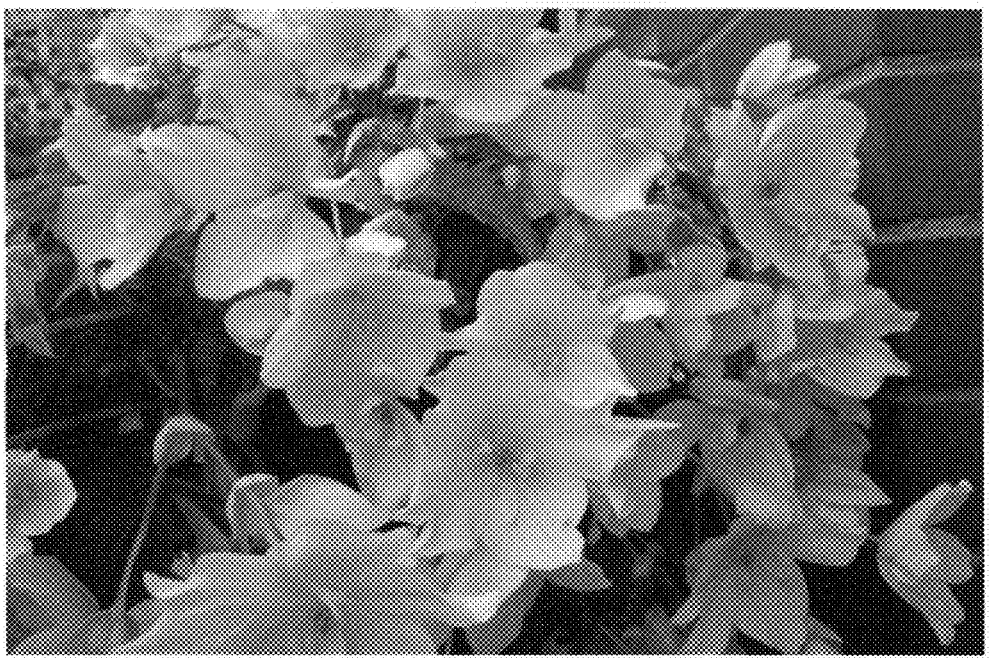
Figure 2:
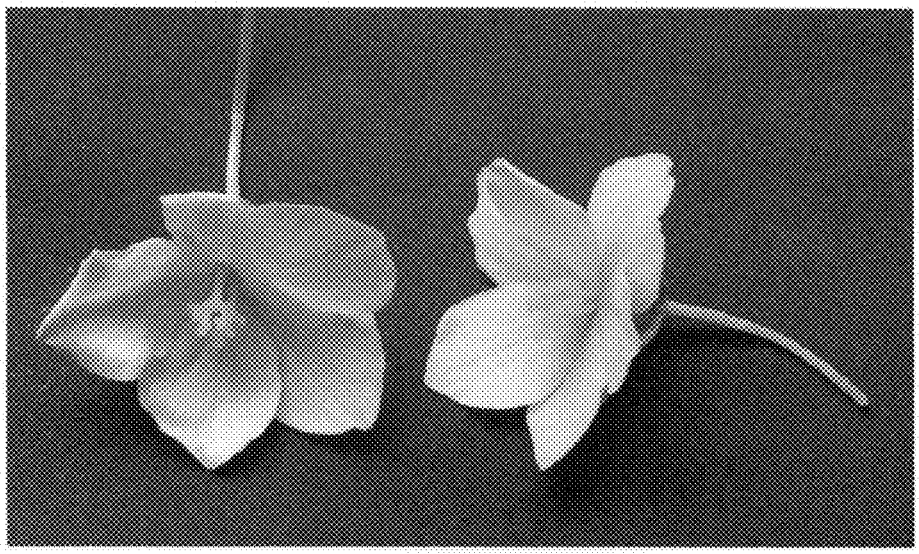
Figure 3:
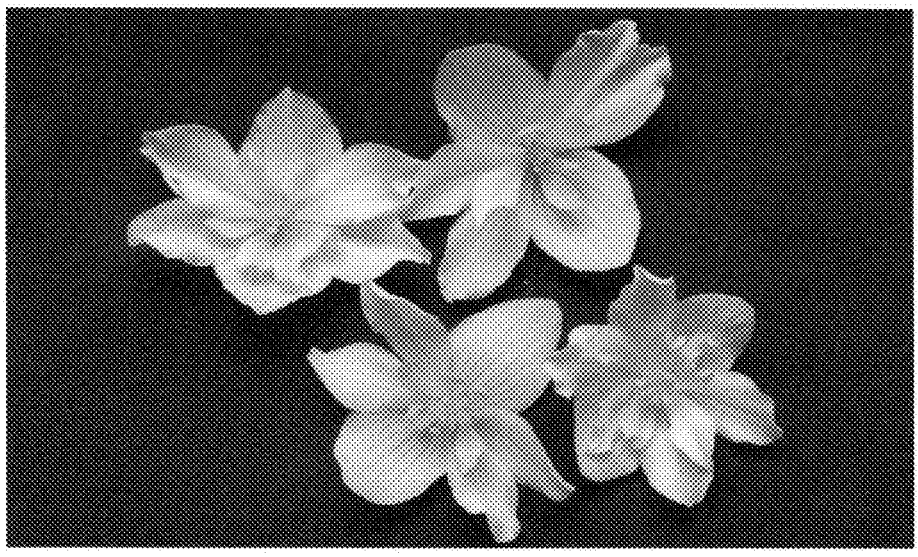

The photographs in FIG. 2 and FIG. 3 were taken of plant parts of plants approximately three months in age (4 cuttings per 15-cm container) that were grown in an unheated greenhouse under ambient light in Naaldwijk, The Netherlands. The photograph in FIG. 2 provides a close-up view of the female flowers of 'YASPYELL'. The photograph in FIG. 3 provides a close-up view of the semi-double male flowers of 'YASPYELL'.

The colors in the photograph may differ slightly from the color values cited in the detailed botanical description, which accurately describe the colors of the new *Begonia*.

DETAILED BOTANICAL DESCRIPTION OF THE PLANT

The following is a detailed description of plants of the new cultivar approximately three months in age (4 cuttings per 15-cm container) as grown in an unheated greenhouse with ambient light in Naaldwijk, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Plant type*.—Deciduous tuberous perennial, grown primarily for use in baskets and containers.

*Plant habit*.—Compact and well-branched habit without cane production in its first year of growth.

*Flowering period*.—From May to October in Congleton, Cheshire, United Kingdom.

*Height and spread*.—Reaches about 40 cm in height and about 35 cm in spread (4 cuttings in a 30-cm container.

*Cold hardiness*.—U.S.D.A. Zone 10.

*Diseases and pests*.—No susceptibility or resistance to diseases or pests has been observed.

*Root description*.—Fleshy to fibrous.

*Growth rate*.—Semi-vigorous.

*Propagation*.—Stem tip cuttings.

*Root development*.—10 to 14 days to initiate roots and 6 to 8 weeks to produce a young rooted plant.

Stem description:

*Stem size*.—Average of 30 cm in length and 8 mm in diameter with lateral branches about 5 mm in diameter.

*Stem shape*.—Round, solid.

*Stem color*.—146D unexposed side, 180C exposed side.

*Stem surface*.—Smooth, and covered with a few colorless hairs, lenticels absent.

*Internode length*.—Up to 60 mm.

*Branching habit*.—Freely branching.

*Branching angle at emergence*.—Approximately 30° to horizontal.

Foliage description:

*Leaf shape*.—Lanceolate, strongly asymmetric with one side narrowly ovate and the other side is narrowly cordate and wider.

*Leaf division*.—Entire.

*Leaf base*.—Cordate.

*Leaf apex*.—Acuminate.

*Leaf venation*.—Pinnate, color 139B on upper surface and 138B on lower surface.

*Leaf margins*.—Irregular serrate with short bristles emerging from tips of the teeth.

*Leaf attachment*.—Petiolate.

*Leaf arrangement*.—Alternate.

*Leaf surface*.—Upper surface; slightly glossy and covered with very occasional scattered short colorless hairs, lower surface; slightly glossy and covered with very occasional scattered short colorless hairs.

*Leaf color*.—Upper surface; 139A, lower surface; 138B, variegation absent.

*Leaf size*.—Average of 11.5 cm in length and 4 cm in width.

*Leaf fragrance*.—None.

*Petioles*.—Up to 3.8 cm in length and 2 mm in diameter, 173D in color, surface is sparsely pubescent with simple translucent hairs.

*Stipules*.—Narrowly triangular in shape, 149D and rapidly becoming dry and papery, about 5 mm in length and 3 mm in width.

Flower description:

*Inflorescence type*.—2 to 3 flowered cymes produced sequentially in the axils of the upper leaves, monoecious.

*Inflorescence number*.—Up to 15 per flowering stem.

*Peduncles*.—Up to 5.5 cm in length and 2.5 mm in diameter, color; 149D, 150D where exposed, surface texture is glabrous (pubescence absent).

*Flower persistence*.—Self-cleaning.

*Flower type*.—Male flowers semi-double, female flowers single (with one or two extra tepals).

*Flower longevity*.—An average of 10 to 14 days depending on conditions.

*Flower fragrance*.—None.

*Flower number*.—3 per inflorescence, up to 12 per stem.

*Flower aspect*.—Upward and outward.

*Bracts*.—2, rounded to reniform in shape, obtuse apex, up to 9 mm in length and 1.3 cm width, 149D, flushed with 35C where exposed, covered with bristly hairs on upper part of margin.

Male flowers:

*Pedicels*.—Up to 2.8 cm in length and 1.5 mm in diameter, color; 149D, 150D where exposed.

*Flower buds*.—Flattened broad ovoid in shape, up to 1.9 cm in length and 1.2 cm in diameter, color is 145C, glabrous and smooth surface texture.

*Flower size*.—Up to 3 cm in length and 6.5 cm in width.

*Flower shape*.—Cupped to flared.

*Flower aspect*.—Facing horizontally.

*Tepals*.—Outer tepals; 2, broad ovate in shape, obtuse apex, rounded base, average of 3.5 cm in length and 2.8 cm in width, glabrous and smooth surface, entire margin, color; outer surface is 9D, 4D at the base, inner tepals; 3 to 5 together with extra petals of various shape and size formed from adapted stamens, obelliptic to narrow obelliptic in shape, obtuse apex, cuneate base, up to 3.5 cm in length and 1.4 cm in width, surface is glabrous and smooth on both surfaces, entire margin, color; ranging between 9D and 4D, 8C at the base.

*Perianth form*.—Flared, tepals are un-fused.

*Stamens*.—3 to 12, obelliptic, some twisted, up to 2.2 cm in length and 1 cm in width, 8A in color.

*Filaments*.—Up to 4 cm in length, 0.5 mm in width, 4C in color.

*Anthers*.—Elliptic in shape, 1 mm in length, <1 mm in width and 14B in color.

*Pollen*.—Moderate to sparse in quantity and 8D in color.

Female flowers:

*Pedicels*.—Average 3.5 cm in length and 1.5 mm in width, 149D, 150D where exposed.

*Flower buds*.—Flattened ovoid in shape, about 2 cm in length and 1.3 cm in diameter, color is 145C, glabrous and smooth surface texture.

*Flower size*.—About 3 cm in length (excluding ovary) and 5 cm in width.

*Flower shape*.—Flared to cupped.

*Flower aspect*.—Facing horizontally.

*Tepals*.—Outer tepals; 2, ovate to broad ovate in shape, obtuse apex, rounded base, average of 2.7 cm in length and 2.3 cm in width, glabrous and smooth surface, entire margin, color; outer surface between 9C to 9D, occasionally suffused with 31C, inner surface 8B to 8C, inner tepals; 3 to 4, broad elliptic to ovate in shape, obtuse apex, cuneate base, up to 2.6 cm in length and 1.7 cm in width, glabrous and smooth surface, entire margin, color; outer surface 9C to 9D, inner surface 8B, 8A at base.

*Perianth form*.—Flared, lepals ale un-fused.

*Styles*.—3 in number, cylindrical, connate at base for <1 mm, up to 3 mm in length and 1 mm in diameter and 14C to 14D in color.

*Stigmas*.—Bifid in shape, stigmatic surfaces twisted around extensions of the style, lobes about 3 mm in length and 1 mm in diameter, 14B in color.

*Ovaries*.—Inferior, triangular in cross section with angles unequally winged, about 9 mm in length and 7 mm in width (excluding wings), color is 144B to 144C.

*Seed*.—No seed, capsules fall before fully ripening.

It is claimed:

1. A new and distinct cultivar of *Begonia* plant named 'YASPYELL' as herein illustrated and described.

* * * * *